United States Patent [19]

Tariq et al.

[11] Patent Number: 5,551,022
[45] Date of Patent: Aug. 27, 1996

[54] NODAL TREE DATA STRUCTURE FOR STORING, CONSOLIDATING, AND DISPLAYING MICROBIOLOGICAL LABORATORY RESULTS

[75] Inventors: M. Hasan Tariq; Michael R. Ostler, both of Tempe, Ariz.

[73] Assignee: Motorola, Inc., Schaumburg, Ill.

[21] Appl. No.: 272,450

[22] Filed: Jul. 11, 1994

Related U.S. Application Data

[63] Continuation of Ser. No. 980,082, Nov. 23, 1992, abandoned.

[51] Int. Cl.$^6$ .................................................. G06F 17/30
[52] U.S. Cl. ................. 395/600; 364/413.02; 364/282.1; 364/224.6; 364/974; 364/922.2
[58] Field of Search ...................... 395/600; 364/413.01, 364/413.02

[56] References Cited

U.S. PATENT DOCUMENTS 4,315,309  2/1982  Coli .................................. 364/413.02

(List continued on next page.)

OTHER PUBLICATIONS

Edward D. Hobart, "A Pathology Reporting System", Computers inHealthcare, vol. 9, No. 7, 15 Jun. 1988, pp. 26–27.
Anonymous, "HP, Digital Assess MUMPS' Validity", Computers inHealthcare, vol. 11, No. SPEISS, 15 Jun. 1990, pp. 4–5.
Michael L. Laughlin, "DOD Plunges Ahead With Embattled HealthcareSystem", Computers in Healthcare, vol. 13, No. SPEISS, 15 Jun. 1992, pp. 8–10.
Proceedings of Computers–Based Medical Systems, IEEE Press New York, 26 Jun. 1989, Minneapolis, MN, pp. 76–80, J. C. Lusth and A. K. Bhatt, "An Embedded Knowledge-–Based System for Interpreting Microbiology Data".
Proceedings of the 12th Annual International Conference of the IEEE/EMBS, IEEE Press New York, 1 Nov. 1990, Philadelphia, PA, vol. 12, No. 3/5, pp. 1210–1211, L. K. Blach et al., "An Application of Computers in a Bacteriological Laboratory".
Proceedings of the 11th Annual Northeast Bioengineering Conference, 14 Mar. 1985, Worcester, MA, pp. 16–19, D. C. Bartoletti et al, "Design of a Cardiovascular Drug Knowledge Base for Use in Critical Care Monitoring".
Computers in Cardiology, IEEE Press New York, 7 Oct. 1986, Boston, MA, pp. 81–84, A. Pierges et al, "Medical Knowledge Organizing System for Planning and Explanation of Drug Interventions".
Journal of Clinical Pathology, vol. 38, No. 2, Feb. 1985, UK, pp. 215–221, R. Ashley, "Microcomputer System for Multistep Specimen Processing and Reporting in a Microbiology Laboratory".
Proceedings of Medical Informatics Europe 78, Springer Verlag Germany, 4 Sep. 1978, Cambridge, UK, pp. 509–519, D. R. Mace, "A Common Approach to a Variety of Clinical Laboratories".
Proceedings of AAMSI Congress, American Association of Medical system and Informatics, US, 2 May 1983, San Francisco, CA, pp. 117–120, W. H. Chamberlin et al., "Data–Base Management of Microbiology Data in an ICU".
Proceedings of the Sixth International Conference on Data Engineering, IEEE Press, New York, 5 Feb. 1990, Los Angeles, CA, pp. 410–419, J. P. Held et al., "A Shared Conceptual Schema for Four Medical Expert Systems".

*Primary Examiner*—Thomas G. Black
*Assistant Examiner*—Paul R. Lintz
*Attorney, Agent, or Firm*—S. Kevin Pickens

[57] ABSTRACT

A method for building and storing a nodal tree structure and a composite display matrix from laboratory information which includes specimen, organism, and drug sensitivity information. The method consolidates microbiological lab results by building the composite display matrix based on the lab results and the relationships among specimens, organisms, and drugs tested. The method also displays the composite display matrix once the lab results are consolidated and the composite display matrix built.

11 Claims, 6 Drawing Sheets

U.S. PATENT DOCUMENTS

| | | | |
|---|---|---|---|
| 4,453,220 | 6/1984 | Flegal et al. | 364/413 |
| 4,733,354 | 3/1988 | Potter et al. | 364/415 |
| 4,847,764 | 7/1989 | Halvorson | 364/413.02 |
| 4,878,175 | 10/1989 | Norden-Paul et al. | 364/413.01 |
| 5,072,383 | 12/1991 | Brimm et al. | 364/413.02 |
| 5,077,666 | 12/1991 | Brimm et al. | 364/413.02 |
| 5,189,609 | 2/1993 | Tivig et al. | 364/413.01 |

| | | | 444-44-4444 | | ICU4 |
| --- | --- | --- | --- | --- | --- |
| | | | DAVE | | kg |
| | | | ADMIT PHYSICIAN: | | SURGEON: |

CENSUS   UTILITY

| FLOWSHEET | LABS | RESPIRATORY | | NOTES |
| --- | --- | --- | --- | --- |
| SITE SUMMARY | TIME SUMMARY | ORG VS DRUG | MICRO | |

FORMAT: ORGANISMS VS DRUG INTERACTION MATRIX

| ORGANISMS | GM | IMIPENEN | MAN | MEZLOCIL ⬆ | NITROFUR ⬆ | OXA |
| --- | --- | --- | --- | --- | --- | --- |
| VIRIDANS STREPTOC ⬆<br>Lower respiratory<br>08/01/90 10:40 | 285 | | | SENSIT ⬆ | | |
| NEISSERIA SPECIES<br>Lower respiratory<br>08/01/90 10:40 | | | | | | |
| STAPAYLOCOCCUS,C ⬆<br>Urine culture<br>08/01/90 11:00 | | SENSIT ⬆ | | | SENSIT ⬆ | |
| ENTEROCOCCUS<br>Urine culture<br>08/01/90 11:00 | | | | SENSIT ⬆ | SENSIT ⬆ | |
| STAPAYLOCOCCUS,C ⬆<br>Urine culture<br>08/01/90 11:10 | | SENSIT ⬆ | | | SENSIT ⬆ | |
| ENTEROCOCCUS<br>Urine culture<br>08/03/90 11:10 | | | | RESIST ⬆ | SENSIT ⬆ | |

FIG. 7

NODAL TREE DATA STRUCTURE FOR STORING, CONSOLIDATING, AND DISPLAYING MICROBIOLOGICAL LABORATORY RESULTS

This application is a continuation of prior application Ser. No. 07/980,082 filed Nov. 23, 1992, now abandoned.

FIELD OF THE INVENTION

This invention relates generally to computer automated and networked, multipatient monitoring and assessment information systems and in particular, to a method for storing, consolidating, and displaying results of microbiological laboratory testing including how particular organisms react to specific drugs.

BACKGROUND OF THE INVENTION

When a patient is admitted to a hospital, a variety of tests are performed on the patient to help in diagnosing the patient's illnesses. Some of the tests include collecting specimens, such as blood, skin samples or urine, for example, from the patient and sending them to a laboratory to be tested. Individual or dissected specimen samples are then tested or grown in cultures to form particular organisms. Specific antibiotic therapeutic drugs are chosen to determine how the organism will react to the drug. A list of antibiotics tested for effectiveness against the organisms is determined which will aid the physician in prescribing the most effective antibiotic.

Currently, an attending physician reviews individual microbiological laboratory results from numerous and different charts which may be spread out over many separate pages. The physician has to determine which drugs and therapy regimen to prescribe to a patient by searching for, correlating and analyzing the various information contained within the charts on different pages. The physician has to try to find what organisms of what particular specimens react favorably to what drugs. Once the physician analyzes the information, the patient treatment plan is formulated, ordered and implemented, and the patient is monitored and evaluated on a regular basis with an ongoing charting process. Further tests and revised drug regimens or dosages may be ordered and reported, resulting in additional or modified data entered in the patient's chart. Hence, the patient's chart is continually being revised and updated at various time intervals wherein the physician must again review and analyze all previous and new data on a regular basis. This repetitive charting process may require the input of several clinicians, specialty health care professionals and physicians as well as the primary or attending physician. Even if the charts are entered into a computer, the physician must flip through the various charts electronically and analyze the results in a manner similar as if handwritten charts were used.

In performing the task of analyzing the information on the laboratory charts, the physician has at least three problems in forming the treatment regime. First, the laboratory results are reported at different times. The specimens are collected, and related information is reported first, followed by the reporting after several days or weeks of what organisms were grown, and lastly by what drugs are effective against the organisms reported. Typically, these lab reports contain a listing of specific drugs and their corresponding sensitivities for any specimen collected and organisms grown during a culture. As there may be multiple organisms grown from a single or dissected specimen culture, each organism detected and tested will have its own listing of specific drug sensitivities on a single chart. Therefore, the laboratory results could be spread out over many singular, successive and separate laboratory reports and over many days which takes valuable time for the physician to organize before analysis of the results begin.

Second, there is no guarantee that the laboratory results will reach a patient's bedside chart before the physician analyzes the results. For example, the laboratory may perform the required tests late one day, so that they are not delivered to the patient's bedside chart until after the physicians finished their rounds the next day. This late delivery of the laboratory results may make the physician's analysis inaccurate, because the analysis was based on incomplete and obsolete record information. This hinders the physician in prescribing an effective treatment plan to improve the condition of the patient.

Third, once the laboratory results reach the patient's bedside chart, the physician must still find which chart is the most recent and try to determine whether there is a change of the reaction of the organism to a drug over a period of time. This information is not readily presented on one chart.

Therefore, there exists a significant need for storing, consolidating, and displaying interactions among various drugs, organisms and specimens based on the most current laboratory results, so that a physician can readily prescribe effective treatment to combat the illnesses suffered by a patient.

SUMMARY OF THE INVENTION

The present invention has utility in storing, consolidating, and displaying both newly entered and modified laboratory information including test results. The composite display matrix displays the essential relationship among drugs and organisms which enables the attending physician and other health care personnel to review, analyze, and more readily determine which drug to prescribe to a sick patient.

Thus, it is an advantage of the present invention to store, consolidate, and display laboratory results showing drugs, organisms and specimens and their interactions to a health care professional on any networked workstation.

It is another advantage of the present invention to provide microbiological information which represents a listing of all antibiotic drugs tested for specific effectiveness against organisms grown.

Yet another advantage of the present invention is to provide information about the sensitivity of an individual organism of a particular specimen to a number of different drugs, the sensitivity of a given organism to a specific drug across a number of similar specimens collected at different times, the effect that a single drug has on multiple organisms in multiple specimen types, and the sensitivity of a set of organisms from a single specimen to a drug.

Another advantage of the present invention is to list organisms according to when they were collected, and which organisms are present within any given specimen, and to suppress any sensitivity measurements which are not needed.

It is also an advantage of the present invention to display the drugs alphabetically.

An advantage of the present invention is that it maximizes the productivity of health care professionals by providing disease tracking information which enhances the level of care for a patient.

Another advantage of the present invention is that it significantly reduces the cost of microbiological record keeping and interpretation by eliminating manual laboratory charting reports.

This invention automates the clinical microbiological charting process and makes all of the patients' charts accessible at any time from several bedside workstations and the laboratory computer even while others are accessing, reviewing or modifying the data. According to one aspect of the invention, a method is provided for displaying lab data contained in a lab report in a composite display matrix on a display monitor. The method is executed by a computer as part of a computer program. The lab data is entered into a lab computer. The lab computer is coupled to the computer. The lab report is received by the computer from the lab computer. The method comprises the steps of: (a) storing the lab data in a nodal tree structure by determining relationships among the lab data and storing the lab data and the relationships in the computer, if the lab data is not stored in the computer; (b) consolidating the lab data into the composite display matrix by arranging and combining the lab data based on the relationships between the lab data; and (c) displaying the composite display matrix on the display monitor.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

FIG. 7 shows an actual composite display matrix in accordance with a preferred embodiment of the invention.

DESCRIPTION OF THE PREFERRED EMBODIMENTS

Figure 1:
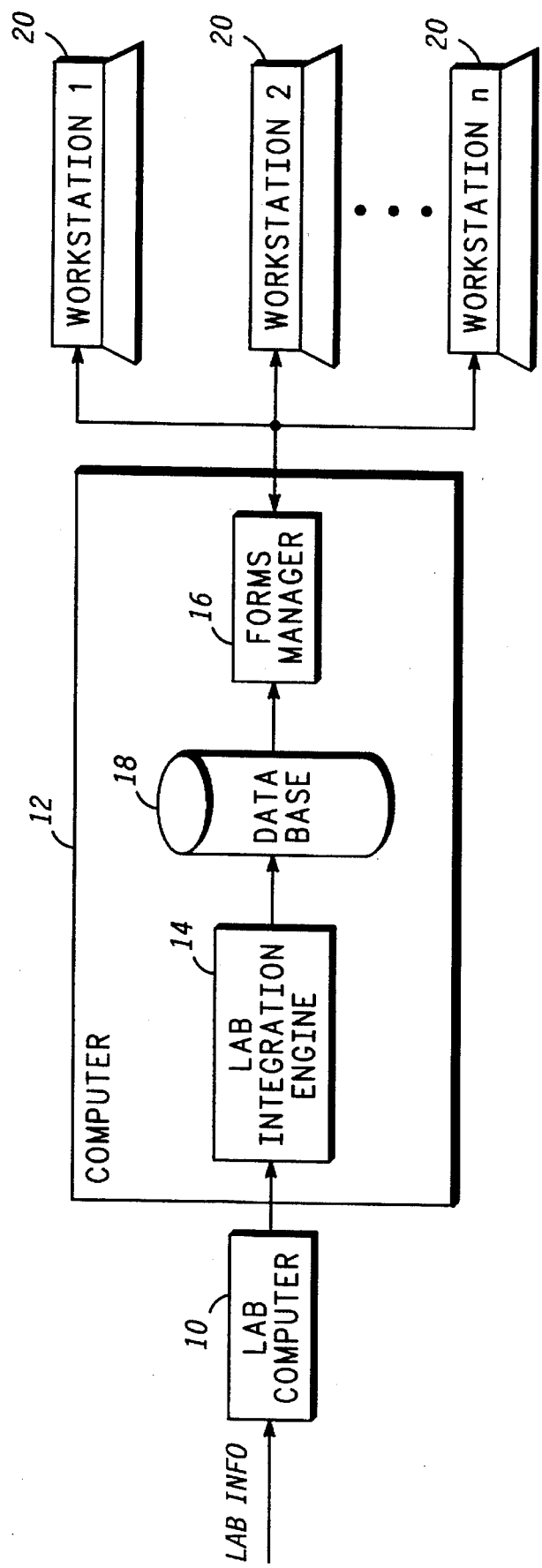
FIG. 1 shows a block diagram of the hardware and software configuration for storing, consolidating, and displaying microbiological laboratory results in accordance with a preferred embodiment of the invention.

As shown in FIG. 1, microbiological test reports or lab reports are entered into the laboratory computer 10 and sent to a computer 12. A laboratory information integration engine 14 within the computer 12 parses, validates, consolidates, and stores the information in a database 18. When a physician selects and opens the "Organism v. Drug Interaction Matrix" form on one of the workstations 20, the forms manager 16 in the computer 12 retrieves the desired information from database 18 and transmits the information to the workstation 20 where it is displayed.

The laboratory computer 10, the computer 12 and workstations 20 each is a commercially available SUN Sparcstation™ running the UNIX™ environment. This invention will execute using most commercially available computer systems including IBM, for example. Moreover, the laboratory computer and the workstations 20 can be connected remotely to the computer 12 using any compatible commercially available network technology.

The lab enters patient information into the lab computer 10 including such information as patient ID number, patient name, specimen description, organisms grown, amount of individual drugs tested on specific organisms and the reaction of the organism to the drugs. The information is transmitted to the computer 12 where the laboratory integration engine 14 stores and consolidates the information according to the flowchart shown in FIG. 2.

Figure 2:
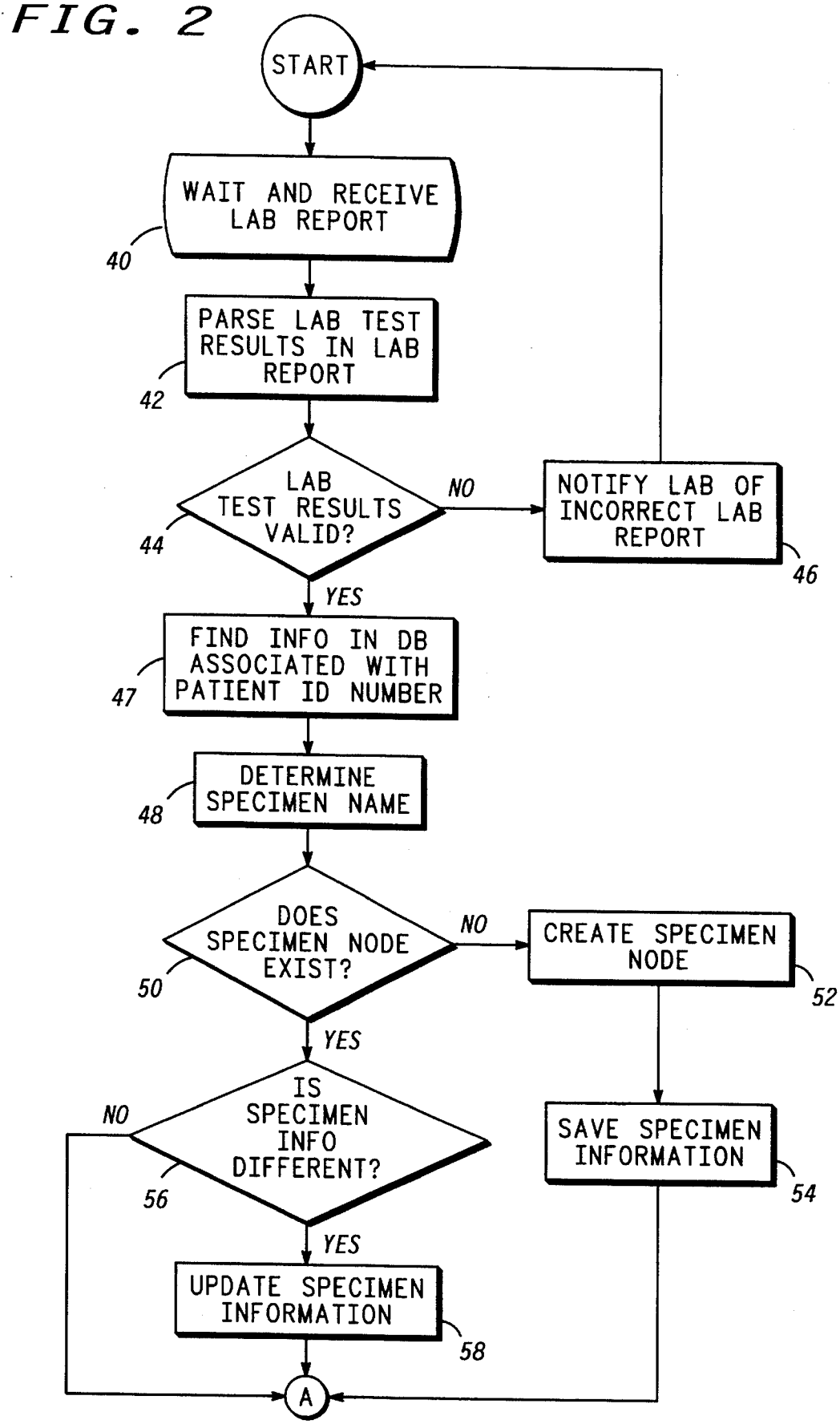
FIGS. 2–4 show a single flowchart of the steps executed by a lab integration engine in accordance with a preferred embodiment of the invention.
Figure 3:
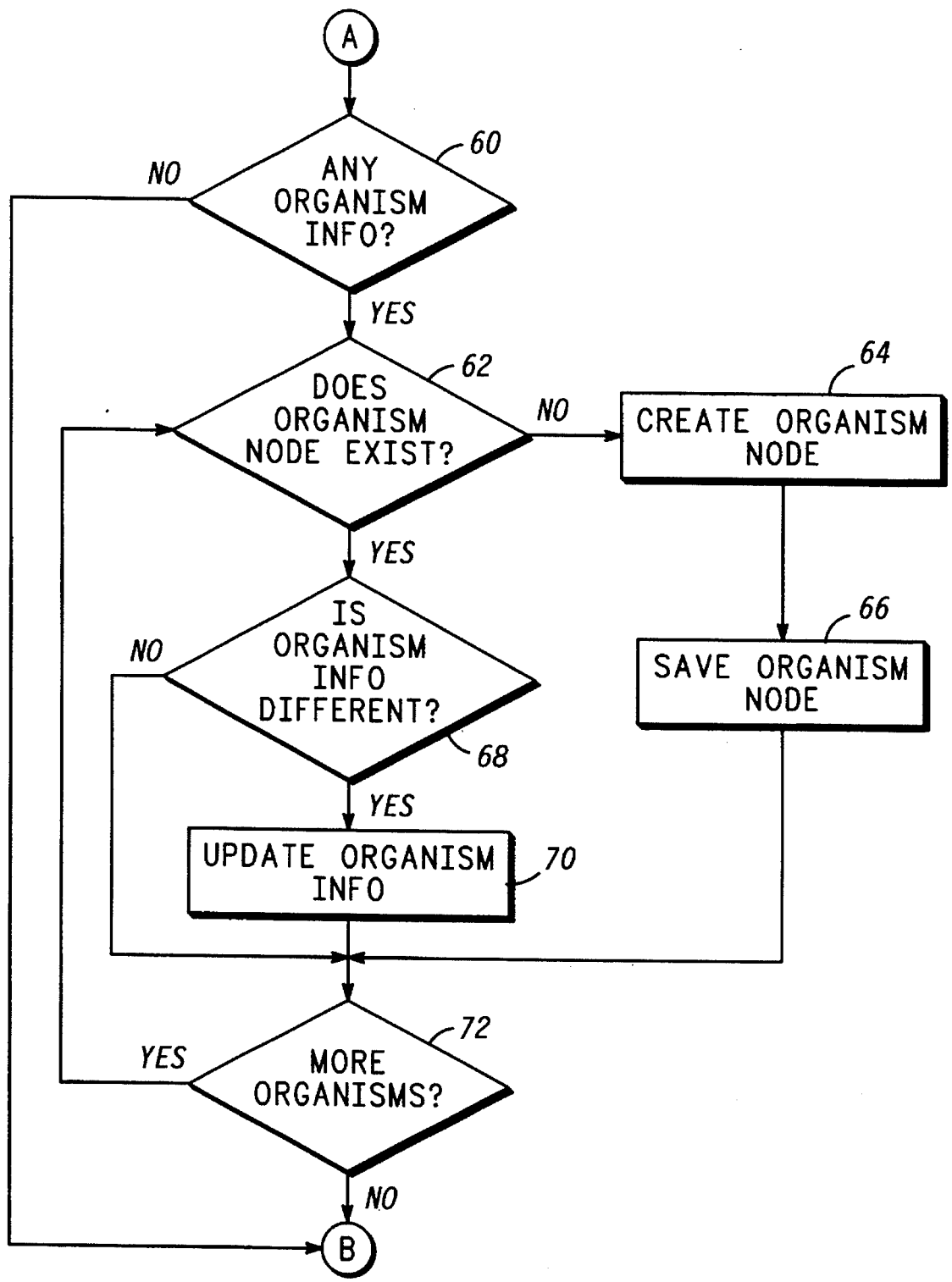
Figure 4:
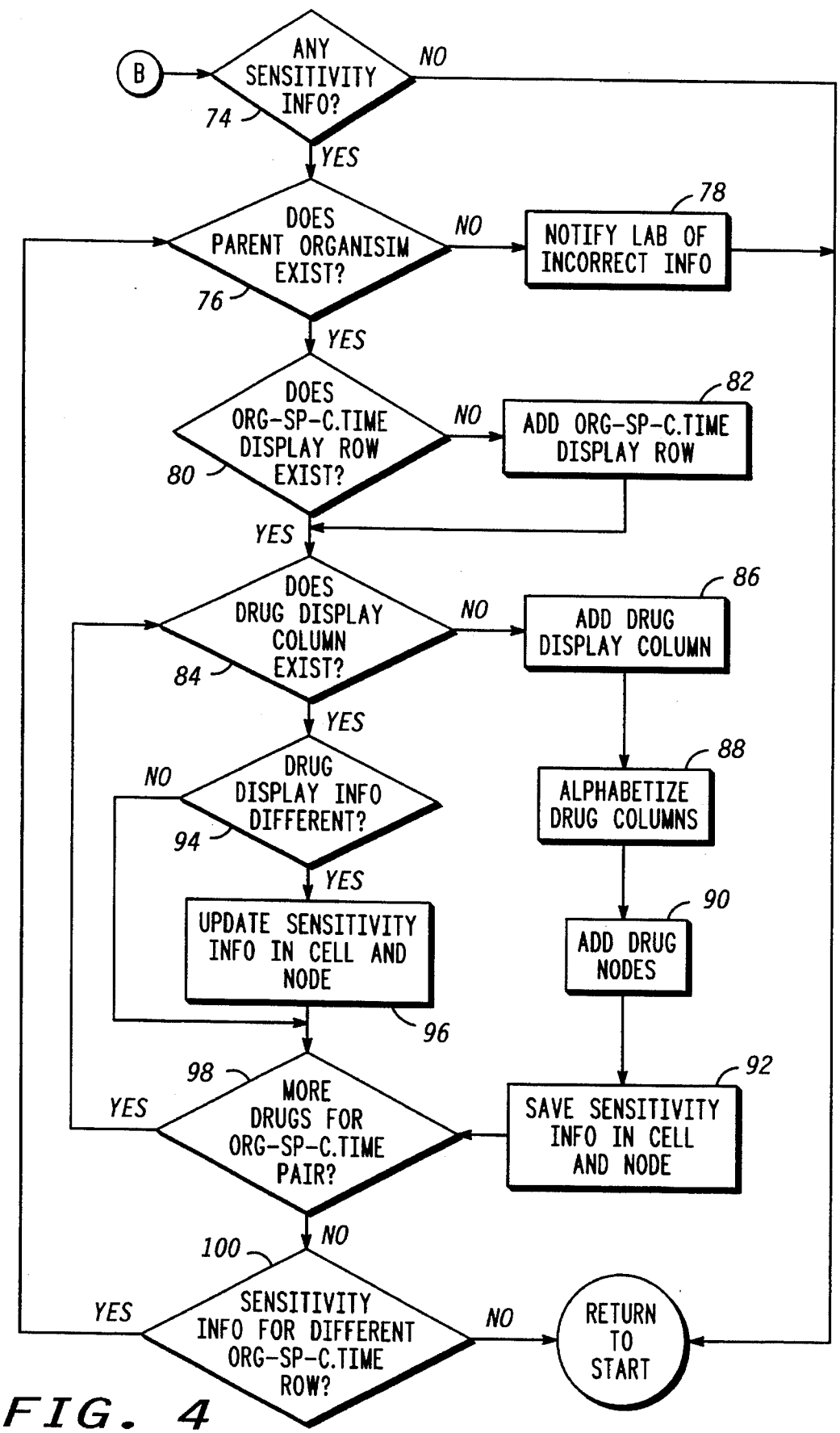
Figures 5, 6:
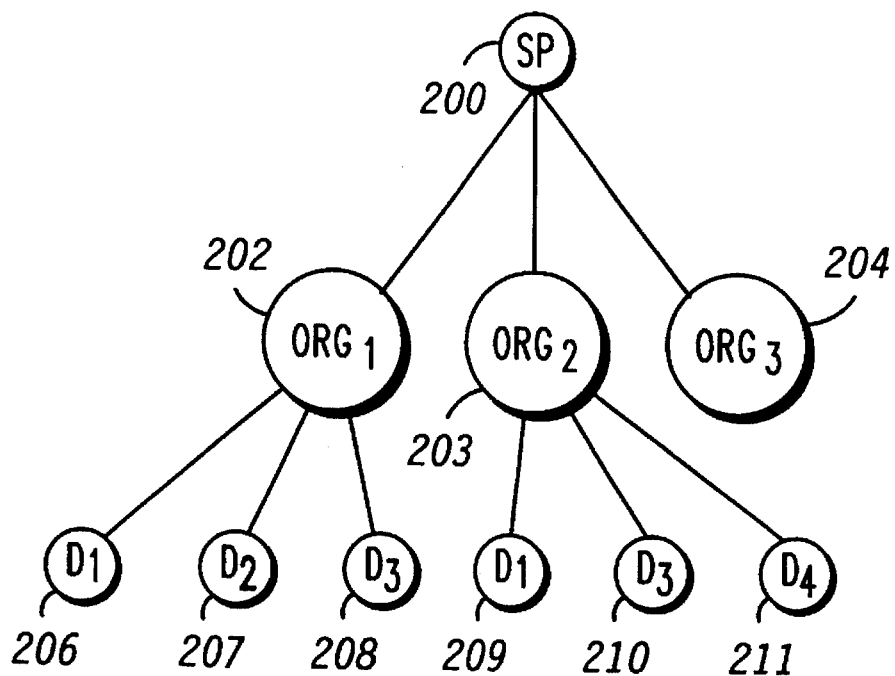
FIG. 5 shows a hierarchical nodal structural relationship of how specimens, organisms, and drugs are related to each other and are stored in a database in accordance with a preferred embodiment of the invention.
FIG. 6 shows a composite 2 rows, 4 column display matrix in accordance with a preferred embodiment of the invention.

FIGS. 2–4 show a flowchart of the steps executed by a lab integration engine in accordance with a preferred embodiment of the invention. The goal of the steps shown in the flowchart of FIGS. 2–4 is to create a specimen-organism-drug nodal structure as shown in FIG. 5 and a composite interaction display matrix as shown in FIG. 6.

According to FIG. 2, laboratory integration engine 14 waits to receive microbiology test result reports from the remote laboratory workstation 10 in step 40. A single lab report will contain information on only a single specimen. Another lab report will have to be generated for reporting on the organism and drug results from a different specimen. Once a lab report is entered into the remote lab computer 10 and received by the computer 14, the integration engine 14 then parses the received information in step 42 to determine the required fields and parameters such as patient ID number, specimen name, collection site, collection time, and order number, for example.

The parsed parameters from the lab report are also passed through a series of validity checks in step 44 to determine whether they are correct. For example, the patient's ID number is compared to a list of IDs for all registered patients in a hospital. If an error occurs in the lab report, the laboratory is notified of an incorrect or invalid lab report in step 46, and the lab integration engine 14 returns to step 40 until another laboratory report is entered and sent by the lab.

Once data from the lab report is parsed and the lab report information validated in steps 42 and 44, respectively, the lab integration engine 14 determines or reads in step 47 the patient ID number as reported in the received lab report. Using the patient ID number, the lab integration engine 14 searches the database 18 in step 47 to find where laboratory information is stored for the particular patient. The lab integration engine 14 thus knows where specific laboratory information as well as other information about a specific patient is stored in the database 18.

According to FIG. 2, once the patient ID number is entered or checked, the lab integration engine 14 reads the lab report to determine in step 48 what specimen is being reported on by the laboratory. After determining what specimen is involved, the lab engine 14 searches the the information stored in the database 18 for the particular patient to determine in step 50 whether a specimen node exists which contains the specimen name and related information. A node, as commonly understood in computer science, is an entity where information, such as a microbiology laboratory report for example, is associated or stored.

If the specimen node does not exist, a specimen node is created in the database 18 in step 52, and all specimen related information is stored in the newly created specimen node in step 54. Specimen information entered into the lab computer 10 and stored in the specimen node includes but is not necessarily limited to specimen descriptions, such as the name of the specimen, collection time, anatomical/bodily collection site (i.e., from where the specimen was taken from the patient), and time of the report, for example.

If the specimen node exists in the database as determined in step 50, which means that the laboratory has reported on it once before, the specimen related information for the particular specimen node is compared with the newly received lab information in step 56. If the newly received lab report information is different, the specimen information stored in the specimen node is updated in step 58. The result of the lab integration engine 14 performing these steps is "SP" (specimen) node 200 shown in FIG. 5.

As shown in FIG. 3, the lab report is checked in step 60 for any organism information including for example, the names of the different types of organisms grown from the specimen, status, entry times, and a measurement number which specifies the concentration of the organism. If there is no organism information in the lab report, the lab integration engine 14 will next check sensitivity information in step 74. Otherwise, the lab integration engine 14 determines whether an organism node exists in step 62 for a particular organism by examining the organism names of the existing organism nodes for the particular organism. If the organism node does not exist, the lab integration engine 14 creates the organism node in step 64 and associates the newly created organism node with the existing specimen node. The lab integration engine saves in step 66 the reported organism information in database 18.

If the organism node is found in database 18, all the organism information is compared in step 68 with the newly received information. If the newly received information is different, the organism node is accordingly updated in step 70 with the new organism information; otherwise, the lab integration engine 14 advances to step 72 to determine whether more organism information is contained in the lab report. If there are additional organisms contained in the lab report, the lab integration engine returns to step 62 to check whether the remaining organism nodes and related information exist within the database 18. The result of the lab integration engine performing these steps is "ORG$_1$", "ORG$_2$", and "ORG$_3$" (organism) nodes 202, 203, and 204, respectively, shown in FIG. 5.

As shown in FIG. 4, if no additional organisms are being reported on by the lab report, the lab report is checked for any appropriate sensitivity information in step 74. Sensitivity information includes measurements about whether a particular organism is reacting to a particular drug. Sensitivity information includes but is not necessarily limited to drug names tested on a specific organism and the resistivity of the organism to the drug. If there is no sensitivity information, then the lab integration engine 14 returns to the beginning to wait for another lab report. Otherwise, the name of the drug and organism upon which the drug was tested are read by the lab integration engine 14 from the lab report.

In step 76 of FIG. 4, the lab integration engine 14 checks to see if a parent organism exists in the database 18 by comparing the organism read from the lab report with each of the organism names stored in the organism nodes. As shown in FIG. 5, a specimen SP is a parent node to organisms ORG$_N$, while organisms are child nodes to the specimen node and a parent to drug nodes D$_N$. Drug nodes are at the bottom of the nodal tree structure and are child nodes to organism nodes. If the parent organism does not exist for a drug being reported on by the lab report, the lab integration engine 14 notifies the lab in step 78 of an incorrect report for an organism not in the database 18 and returns to "start" to wait for another lab report. Steps 76 and 78 are error check steps because all organism nodes are added as child nodes to the specimen node in steps 60–72 of FIGS. 2 and 3 before any information about the drugs is examined and entered.

Once the error check is performed in step 76, the lab integration engine 14 determines whether an organism-specimen pair display row exists in database 18 at a particular collection time in the display matrix shown in FIG. 6. This row will be referred to as an organism-specimen-collection time row. The collection time is when the specimen was collected or taken from the patient rather than when the organism was last examined by the laboratory. The organism-specimen-collection time row will already exist when the lab report is updating the status or the sensitivity information about the reaction of the organism to certain drugs. For example, the collection time of a blood specimen was taken at 10:00 a.m. The initial observation results from the lab are reported although there may not be any drug sensitivity. Therefore, when the laboratory finally observes a reaction of an organism which was grown from the blood specimen to a particular drug, the collection time still remains at 10:00 a.m. although the observation, the organism reaction, and the actual reporting of the organism reaction occurred later.

According to FIG. 4, the lab integration engine 14 will create the organism-specimen-collection time display row in step 82 if it does not exist. Once the organism-specimen-collection time display row is created, the lab integration engine 14 checks to see in step 84 whether there is a drug column existing in the composite display matrix shown in FIG. 6. If the drug column does not exist, a drug column is created and alphabetized with other existing drug columns by the lab integration engine in steps 86 and 88, respectively. Moreover, the lab integration engine 14 creates a drug node in step 90 and associates the drug node with the corresponding organism node as shown in the specimen-organism-drug nodal structure of FIG. 5. The lab integration engine 14 saves in step 92 sensitivity measurements in both the drug node and the display cell where the organism-specimen-collection time row and drug column intersect as shown in FIG. 6.

When a drug column is created, it is created across all other existing organism-specimen-collection time rows even though there is no sensitivity information available for the different organism-specimen pairs at the present time. However, information about the reaction of the drug on different organism-specimen-collection time rows may be reported on in the future.

A display cell is created in each of the rows when the drug column is created. Therefore, as shown in FIG. 6, when drug column D$_1$ is created, it creates a display cell in each of the organism-specimen-collection time rows. The purpose of creating the drug column across different organism-specimen-collection time rows is to visually consolidate the interrelationship of how different organism-specimen pairs react to one particular drug.

According to FIG. 4, if a drug column already exists, the lab integration engine 14 examines in step 94 whether the sensitivity information is different in the drug display cell than what is being reported in the lab report. If it is different, then both the drug node and drug display cell are updated with the new sensitivity information in step 96. If it is not different, the lab report is further examined by the lab integration engine 14 in step 98 to determine whether more drugs are being reported for this particular organism-specimen pair. Sensitivity information about a particular organism or all drugs tested on the particular organism is provided in a lab report before sensitivity information about another organism is provided. If more sensitivity information is available, then the lab integration engine 14 returns to step 84 and executes until all drug sensitivity information for one particular organism has been entered.

When all drug sensitivity information for one particular organism has been entered, the lab report is checked by the lab integration engine 14 in step 100 to determine whether there is further drug sensitivity information for different organism-specimen pairs. If there is, then the lab integration engine 14 repeats from step 76 until all information has been read and consolidated in the nodal structure shown in FIG. 5 and the composite display matrix shown in FIG. 6.

The end result of the lab integration engine 14 executing the steps shown in the flowchart of FIGS. 2–4 is the hierarchical nodal structure shown in FIG. 5 and a composite display matrix as shown in FIG. 6.

FIG. 5 shows a hierarchical nodal structure relationship of how specimens, organisms, and drugs are related to each other and are stored in a database in accordance with a preferred embodiment of the invention. In FIG. 5, nodes representing specimen SP, organism $ORG_N$, and drug $D_N$ entities are linked in a form that represents the hierarchical relationship among them. At the top, a specimen node 200 contains all the specimen related information. Organism nodes 202–204 are created as organisms $ORG_N$ are grown and reported in culture batteries. As the organisms are tested for sensitivity to certain sets of drugs, the sensitivity results are stored within corresponding drug nodes 206–211. Organism 204 has not been tested for its sensitivity to any drugs, and therefore there are no child drug nodes. FIG. 5 represents a typical hierarchical nodal structure for one specimen and is for illustrative and narrative example only.

FIG. 6 shows a composite 2 row, 4 column display matrix in accordance with a preferred embodiment of the invention. In the composite display matrix shown in FIG. 6, two organism-specimen-collection time rows are shown as well as four drug columns. This display matrix comprises eight display cells. The two organism-specimen-collection time rows represent the organism 202, specimen 200 pair as well as the organism 203, specimen 200 pair, respectively. The composite display matrix of FIG. 6 does not show the organism 204, specimen 200 pair because this organism-specimen pair was not tested for sensitivity to various drugs. Although there are four drug columns shown in FIG. 6, only three drugs were tested against each organism as shown in FIG. 5. For example, drug D1 (first column in display matrix) stored in drug nodes 206 and 209 is the same drug tested against different organism-specimen pairs. Similarly, drug D3 stored in drug nodes 208 and 210 is the same drug tested against two different organism-specimen pairs. Drugs D2 and D4 stored in drug nodes 207 and 211, respectively, were tested against different organism-specimen pairs. The sensitivity information will only appear in a cell for which information has been provided. Otherwise, the display cell will remain empty or blank. The composite display matrix shown in FIG. 6 is then displayed on a display monitor.

FIG. 6, as well as an actual display shown in FIG. 7, are composite display matrices showing the interaction of different organism-specimen pairs to various drugs for lab reports received at different times. These displays help a physician assimilate which drugs produce favorable reactions in different organism-specimen pairs. This is a concise, consolidated display showing the interrelationship among the different organism reactions to commonly tested drugs. The physician or other health care professional can much more readily discern what drugs to prescribe to a patient from this display than from numerous individual sensitivity lab reports stored electronically or manually.

An actual composite display matrix 250 is shown in FIG. 7. After a physician selects the matrix display form, a forms manager 16 retrieves the structure of the matrix form and the required information from the database 18 as shown in FIG. 1. For example, the composite display matrix 250 is provided whenever the "Micro" (Microbiology) selection 260 is chosen by a physician in the upper "Sections:" 265 menu and the "Org vs. drug" (organism v. drug) selection 270 is chosen in the lower "Forms:" 275 menu using for example, a workstation mouse.

As shown in FIG. 7 in the organism rows 280, each organism, specimen name and specimen collection time is identified within one display cell, for example, display cell 285. Drug columns 290 identify the drugs being tested against organism-specimen pairs for a reaction. Display cells across the row represent a cell for each drug tested against a specific organism-specimen pair. Within this corresponding cell, the appropriate sensitivity information is displayed as either a Minimum Inhibitory Concentration (MIC) value, a Kirby-Bauer (KB) measurement or other spedfied mensuration system value. Moreover, the words "SENSIT" (sensitive) or "RESIST" (resistive) may be displayed within the cell although any other representation is possible.

It will be appreciated by those skilled in the art that the present invention may store and consolidate a vast number of individual, successive clinical microbiological test reports into a single row by column display matrix. Although the composite display matrix displays drug sensitivity information in columns and organism-specimen-collection times in rows, drug information could be displayed in rows while the organism-specimen-collection time could be displayed in columns. What is important is that health care professionals are able to immediately visualize and understand the current status of the laboratory results and drug sensitivity information from the composite display matrix.

What we claim is:

1. A method executed by a computer as part of a computer program for displaying lab data in a composite display matrix on a display monitor, said lab data including data identifying one or more specimens, one or more organisms grown from each specimen, and one or more drugs tested against the organisms for a reaction, the lab data being entered into a lab computer to form a lab report, said lab computer coupled to said computer, said lab report being received by said computer from said lab computer, said method comprising the steps of:

a) determining relationships among said lab data including determining which of the organisms are grown from which of the specimens and which of the drugs are tested against which of the organisms;

b) storing said lab data and said relationships in a nodal tree structure in said computer if said lab data is not already stored in said computer;

c) consolidating said lab data into said composite display matrix by arranging and combining said lab data based on said relationships between said lab data, said composite display matrix having a first dimension for each of said organisms grown for each of said specimens, a second dimension for each of said drugs tested against any of said organisms, and a cell at each of a number of different coordinate combinations of said first and second dimension, said cell containing drug sensitivity information indicating sensitivity of said organisms to said drugs; and d) displaying said composite display matrix on said display monitor.

2. A method as recited in claim 1, wherein said lab data comprises specimen information including a specimen name, organism information including a plurality of organism names, and said drug sensitivity information including a plurality of drug names, and wherein step (b) further comprises the steps of:

(b1) creating a specimen node;

(b2) storing specimen information in said specimen node;

(b3) creating a plurality of organism nodes and associating each of said organism nodes with said specimen node;

(b4) storing in a corresponding one of said organism nodes said organism information associated with each of said organism names;

(b5) creating a plurality of drug nodes and associating each of said drug nodes with said corresponding organism node; and (b6) storing in a corresponding one of said drug nodes said drug information associated with each of said drug names.

3. A method as recited in claim 2, wherein step (b) further comprises the step of:

(b7) updating said specimen information, said organism information, and said drug sensitivity information if said specimen, organism, and drug sensitivity information differs from said lab data contained in said lab report.

4. A method as recited in claim 1, wherein said lab data comprises specimen information including a specimen name, and wherein step (b) comprises the steps of:

(b1) determining whether said specimen name is stored in said computer;

(b2) creating a specimen node if step (b1) determines that said specimen name is not stored in said computer;

(b3) storing said specimen information in said specimen node if said specimen node is created in step (b2); and (b4) updating said specimen information stored in said specimen node if said specimen information stored in said specimen node differs from said specimen information contained in said lab data.

5. A method as recited in claim 1, wherein said lab data comprises organism information including a plurality of organism names, and wherein step (b) comprises the steps of:

(b1) determining whether each of said organism names is stored in said computer;

(b2) creating an organism node for each of said organism names which is determined in step (b1) not to be stored in said computer;

(b3) storing said organism information in said corresponding organism node for each of said organism nodes created in step (b2); and (b4) updating said organism information stored in said corresponding organism node if said organism information stored in said organism node differs from said organism information contained in said lab data.

6. A method as recited in claim 1, wherein said lab data comprises said drug sensitivity information including a plurality of drug names, and wherein step (b) comprises the steps of:

(b1) determining whether each of said drug names is stored in said computer;

(b2) creating a drug node for each of said drug names which is determined in step (b1) not to be stored in said computer;

(b3) storing said drug information in said corresponding drug node for each of said drug nodes created in step (b2); and (b4) updating said drug information stored in said corresponding drug node if said drug information stored in said drug node differs from said drug information contained in said lab data.

7. A method as recited in claim 1, wherein said lab data comprises specimen information including a specimen name and collection time, organism information including a plurality of organism names, and said drug sensitivity information including a plurality of drug names, wherein step (c) comprises the steps of:

(c1) creating a display matrix row in said composite display matrix for each combination of said specimen name, said collection time, and each of said organism names;

(c2) creating a display matrix column for each of said drug names; (c3) alphabetizing said display matrix columns created for each of said drug names; and (c4) saving said drug sensitivity information in a display cell where said display matrix row and said display matrix column intersect.

8. A method as recited in claim 1, wherein said lab data comprises specimen information including a specimen name and collection time, organism information including a plurality of organism names, and said drug sensitivity information including a plurality of drug names, wherein step (c) further comprises the steps of:

(c1) creating a display matrix row in said composite display matrix for each combination of said specimen name, said collection time, and each of said organism names if said display matrix row does not exist in said composite display matrix;

(c2) creating a display matrix column for each of said drug names if said display matrix column does not exist in said composite display matrix;

(c3) alphabetizing said display matrix columns created for each of said drug names; and (c4) saving said drug sensitivity information in a display cell where said display matrix row and said display matrix column intersect.

9. A method as recited in claim 1, further comprising the step of:

d) notifying said lab computer of invalid lab data if said lab data contained in said lab report is determined to be invalid.

10. A method executed by a computer as part of a computer program for displaying lab data in a composite display matrix on a display monitor, said lab data being entered into a lab computer to form a lab report, said lab computer being coupled to said computer, said lab report being received by said computer from said lab computer, said lab data comprising specimen information including a specimen name and collection time, organism information including a plurality of organism names, and drug sensitivity information including a plurality of drug names, said method comprising the steps of:

a) determining relationships among said specimen, organism, and drug information;

b) storing said lab data and said relationships in a nodal tree structure in said computer if said lab data is not already stored in said computer;

c) consolidating said specimen, organism, and drug information by building said composite display matrix based on said relationships among said specimen, organism, and drug information, said composite display matrix having a first dimension for each of said organisms grown for each of said specimens, a second dimension for each of said drugs tested against any of said organisms, and a cell at each of a number of different coordinate combinations of said first and second dimension, said cell containing said drug sensitivity information indicating sensitivity of said organisms to said drugs; and d) displaying said composite display matrix on said display monitor.

11. A method executed by a computer as part of a computer program for displaying lab data contained in a lab report in a composite display matrix on a display monitor, said lab data being entered into a lab computer to form a lab report, said lab computer being coupled to said computer, said lab report being received by said computer from said lab computer, said lab data comprising specimen information including a specimen name and collection time, organism information including a plurality of organism names, and drug sensitivity information including a plurality of drug names, said method comprising the steps of:

(a) creating a specimen node;

(b) storing specimen information in said specimen node;

(c) creating a plurality of organism nodes and associating each of said organism nodes with said specimen node;

(d) storing in a corresponding one of said organism nodes said organism information associated with each of said organism names;

(e) creating a plurality of drug nodes and associating each of said drug nodes with at least one of said organism nodes;

(f) storing in a corresponding one of said drug nodes said drug information associated with each of said drug names;

(g) updating said specimen information, said organism information, and said drug sensitivity information if said specimen, organism, and drug sensitivity information differs from said lab data contained in said lab report;

(h) creating a display matrix row in said composite display matrix for each combination of said specimen name, said collection time, and each of said organism names if said display matrix row does not exist in said composite display matrix;

(i) creating a display matrix column for each of said drug names if said display matrix column does not exist in said composite display matrix;

(j) alphabetizing said display matrix columns created for each of said drug names;

(k) saving said drug sensitivity information in at least one display cell which is formed by where one of said display matrix rows and one of said display matrix columns intersect; and (l) displaying said composite display matrix on said display monitor.

* * * * *